United States Patent
Mears et al.

(10) Patent No.: US 9,264,129 B2
(45) Date of Patent: Feb. 16, 2016

(54) HANDHELD DIABETES MANAGER WITH A FLIGHT MODE

(71) Applicant: Roche Diabetes Care, Inc., Indianapolis, IN (US)

(72) Inventors: Mark G. Mears, Westfield, IN (US);
Mark Nierzwick, Brownsburg, IN (US);
Phillip E. Pash, Indianapolis, IN (US);
Vincent R. Rizzo, Indianapolis, IN (US);
Bettina Steiner, Kaiserstuhl (CH);
Kristin M. Westerfield, Indianapolis, IN (US)

(73) Assignee: Roche Diabetes Care, Inc., Indianapolis, IN (US)

(*) Notice: Subject to any disclaimer, the term of this patent is extended or adjusted under 35 U.S.C. 154(b) by 0 days.

(21) Appl. No.: 13/661,156

(22) Filed: Oct. 26, 2012

(65) Prior Publication Data

US 2013/0172709 A1 Jul. 4, 2013

Related U.S. Application Data

(60) Provisional application No. 61/581,149, filed on Dec. 29, 2011.

(51) Int. Cl.
*A61B 5/157* (2006.01)
*H04B 7/26* (2006.01)
(Continued)

(52) U.S. Cl.
CPC ............... *H04B 7/26* (2013.01); *A61B 5/0002* (2013.01); *A61B 5/14532* (2013.01);
(Continued)

(58) Field of Classification Search
CPC  G06F 19/3468; A61B 5/7435; A61B 5/0002; A61B 5/14532; H04W 84/20; H04W 4/001; A61M 5/1723; A61M 2205/35; A61M 2205/3569; A61M 2205/3584
USPC .................. 700/17, 18, 83, 266; 340/539.12; 702/19, 22, 23, 25, 31, 32; 600/365
See application file for complete search history.

(56) References Cited

U.S. PATENT DOCUMENTS 6,893,395 B1 * 5/2005 Kraus ................ A61N 1/37276
600/300
7,912,655 B2 3/2011 Power et al.
(Continued)

FOREIGN PATENT DOCUMENTS

CN 101208700 A 6/2008
CN 102204122 A 9/2011
(Continued)

*Primary Examiner* — Shogo Sasaki
(74) *Attorney, Agent, or Firm* — Harness Dickey (57) ABSTRACT

A handheld diabetes manager has a flight mode that cooperatively interacts with an external medical device and includes a port configured to receive a test strip for blood glucose measurement, a blood glucose measurement module operable with the test strip, a communications module and a user interface module. The communications module selectively communicates wirelessly with an external medical device. The user interface module communicates with the blood glucose measurement module and the communications module and operates to provide a graphical user interface on a display of the diabetes manager. The graphical user interface includes a screen with a flight mode option. When the flight mode option is enabled and the external medical device is paired and currently communicating with the diabetes manager, the user interface module interacts with the communication module to send a command to the external medical device to turn off wireless communication of the external medical device.

9 Claims, 9 Drawing Sheets

(51) Int. Cl.
*A61B 5/00* (2006.01)
*A61B 5/145* (2006.01)
*A61M 5/142* (2006.01)
*A61M 5/172* (2006.01)
*G06F 19/00* (2011.01)
*H04W 4/00* (2009.01)
*H04W 84/20* (2009.01)

(52) U.S. Cl.
CPC ......... *A61B 5/7435* (2013.01); *A61M 5/14244* (2013.01); *A61M 5/1723* (2013.01); *G06F 19/3406* (2013.01); *G06F 19/3468* (2013.01); *H04W 4/001* (2013.01); *A61M 2205/35* (2013.01); *A61M 2205/3569* (2013.01); *A61M 2205/3584* (2013.01); *H04W 84/20* (2013.01)

(56) References Cited

U.S. PATENT DOCUMENTS

| | | |
|---|---|---|
| 7,976,467 B2 | 7/2011 | Young et al. |
| 2005/0038680 A1* | 2/2005 | McMahon ........... A61B 5/0022 705/3 |
| 2005/0267650 A1* | 12/2005 | Carpenter ................ G06F 1/26 701/3 |
| 2007/0123290 A1* | 5/2007 | Stenmark ........... H04W 52/288 455/522 |
| 2008/0287922 A1* | 11/2008 | Panduro .............. G06F 19/3456 604/890.1 |
| 2008/0312585 A1 | 12/2008 | Brukalo et al. |
| 2009/0113295 A1 | 4/2009 | Halpern et al. |
| 2009/0305317 A1 | 12/2009 | Brauer et al. |
| 2010/0052899 A1 | 3/2010 | Bruce |
| 2010/0081911 A1 | 4/2010 | Sloan et al. |
| 2010/0105999 A1 | 4/2010 | Dixon et al. |
| 2010/0198143 A1 | 8/2010 | Estes et al. |
| 2010/0256047 A1 | 10/2010 | Sieh et al. |
| 2010/0292556 A1 | 11/2010 | Golden |
| 2010/0317953 A1 | 12/2010 | Reggiardo et al. |
| 2010/0331654 A1 | 12/2010 | Jerdonek et al. |
| 2011/0152970 A1 | 6/2011 | Jollota et al. |
| 2011/0178717 A1 | 7/2011 | Goodnow et al. |
| 2011/0193704 A1 | 8/2011 | Harper et al. |

FOREIGN PATENT DOCUMENTS

| | | |
|---|---|---|
| EP | 2120173 | 11/2009 |
| WO | WO2009/005957 | 1/2009 |

* cited by examiner

HANDHELD DIABETES MANAGER WITH A FLIGHT MODE

CROSS-REFERENCE TO RELATED APPLICATIONS

This application claims the benefit of U.S. provisional application 61/581,149 filed on Dec. 29, 2011. The disclosure of the above application is incorporated herein by reference in its entirety.

FIELD

The present disclosure relates to a handheld diabetes manager that has a flight mode for an external medical device, such as an insulin pump, communicating with the diabetes manager.

BACKGROUND

Diabetes mellitus, often referred to as diabetes, is a chronic condition in which a person has elevated blood glucose levels that result from defects in the body's ability to produce and/or use insulin. There are three main types of diabetes. Type 1 diabetes usually strikes children and young adults, and may be autoimmune, genetic, and/or environmental. Type 2 diabetes accounts for 90-95% of diabetes cases and is linked to obesity and physical inactivity. Gestational diabetes is a form of glucose intolerance diagnosed during pregnancy and usually resolves spontaneously after delivery.

Diabetes is managed primarily by controlling the level of glucose in the bloodstream. This level is dynamic and complex, and is affected by multiple factors including the amount and type of food consumed, and the amount of insulin (which mediates transport of glucose across cell membranes) in the blood. Blood glucose levels are also sensitive to exercise, sleep, stress, smoking, travel, illness, menses, and other psychological and lifestyle factors unique to individual patients. The dynamic nature of blood glucose and insulin, and all other factors affecting blood glucose, often require a person with diabetes to forecast blood glucose levels. Therefore, therapy in the form of insulin or oral medications, or both, can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information, such as blood glucose, is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates and proteins along with effects of exercise or other physiologic states. The management of lifestyle factors such as body weight, diet, and exercise can significantly influence the type and effectiveness of a therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include patient-owned bG meters, continuous glucose monitors, ambulatory insulin infusion pumps, diabetes analysis software, and diabetes device configuration software. Each of these systems generates and/or manages large amounts of diagnostic and prescriptive data. Personal healthcare devices include weight scales, blood pressure cuffs, exercise machines, thermometers, and weight management software. Patient recorded logs include information relating bG levels, meals, exercise and lifestyle. Lab test results include HbA1C, cholesterol, triglycerides, and glucose tolerance. Healthcare professional recommendations include prescriptions, diets, test plans, therapy changes and other information relating to the patient's treatment.

The present teachings are directed to a handheld diabetes manager that includes a user interface with a travel mode for an external medical device, such as an insulin pump, communicating with the diabetes manager.

SUMMARY

This section provides a general summary of the disclosure, and is not a comprehensive disclosure of its full scope or all of its features.

The present teachings provide a handheld diabetes manager that has a flight mode that cooperatively interacts with an external medical device and includes a port configured to receive a test strip for blood glucose measurement, a blood glucose measurement module cooperatively operable with the test strip, a communications module and a user interface module. The communications module selectively communicates wirelessly with the external medical device. The user interface module is in data communication with the blood glucose measurement module and the communications module and operates to provide a graphical user interface on a display of the diabetes manager. The graphical user interface includes a screen with a flight mode option. When the flight mode option is enabled and the external medical device is paired and currently communicating with the diabetes manager, the user interface module interacts with the communication module to send a command to the external medical device to turn off wireless communication of the external medical device.

The present teachings provide a handheld diabetes manager that has a flight mode that cooperatively interacts with an external medical device and includes a port configured to receive a test strip for blood glucose measurement, a blood glucose measurement module cooperatively operable with a test strip inserted in the port for blood glucose measurement, a bolus advice module, a communications module, a travel module and a user interface module. The bolus advice module is configured to receive blood glucose measurements from the blood glucose measurement module and operates, in response to an input, to compute an insulin recommendation for a patient based in part on the blood glucose measurements. The communications module selectively communicates via a wireless data link with an external medical device. The travel module cooperatively operates with the communications module to effectuate a flight mode. The user interface module is in data communication with the travel module and operates to provide a graphical user interface on a display of the diabetes manager. The graphical user interface includes a travel screen that allows a user to selectively enable or disable a flight mode. The user interface module presents, in response to user input to access recommendation from the bolus advice module may be based on data that is outdated.

The present teachings also provide an alternative embodiment wherein the flight mode option is enabled by sending a flight mode command to the external medical device during a periodic listening window of the external medical device. Periodic listening windows of the external medical device are associated with corresponding periodic beacons from the external medical device to the diabetes manager. In response to the flight mode command from the diabetes manager, the external medical device enters a listening only mode having periodic listening windows without sending beacons.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical "or". It should be understood that steps within a method may be executed in different order without altering the principles of the present disclosure.

Figure 1:
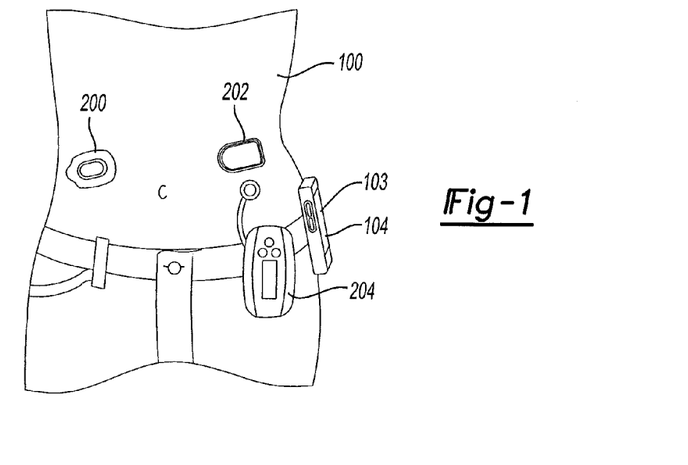
FIG. 1 shows a patient with a continuous glucose monitoring (CGM) patch, an ambulatory durable insulin infusion pump, an ambulatory non-durable insulin infusion pump, and a diabetes manager.

Referring now to FIG. 1, a person with diabetes 100 using various medical devices is illustrated. Persons with diabetes include persons with metabolic syndrome, persons with prediabetes, type 1 diabetes, type 2 diabetes, and gestational diabetes, and are collectively referred to as a patient. Healthcare providers for diabetes are diverse and include nurses, nurse practitioners, physicians, diabetes nurse educators, nutritionists and endocrinologists and are collectively referred to as a clinician.

During a healthcare consultation, the patient 100 typically shares with the clinician a variety of patient data including blood glucose measurements, continuous glucose monitor data, amounts of insulin infused, amounts of food and beverages consumed, exercise schedules, and other lifestyle information. The clinician may obtain additional patient data that includes measurements of HbA1C, cholesterol levels, triglycerides, blood pressure, and weight of the patient 100. The patient data can be recorded manually or electronically on a handheld diabetes management device 104 having a display 103, a diabetes analysis software executed on a personal computer (PC not shown), and/or a web-based diabetes analysis site (not shown). The clinician can analyze the patient data manually or electronically using the diabetes management device 104, the diabetes analysis software and/ or the web-based diabetes analysis site. After analyzing the patient data and reviewing adherence of the patient 100 to previously prescribed therapy, the clinician can decide whether to modify the therapy for the patient 100.

Referring now to FIG. 1, the patient 100 can use a continuous glucose monitoring (CGM) device or CGM patch 200, an ambulatory non-durable insulin infusion pump 202 or an ambulatory durable insulin infusion pump 204 (hereinafter insulin pump 202 or 204), and the handheld diabetes management device 104 (hereinafter the diabetes manager or meter 104). The CGM patch 200 includes a body mount, a reusable component and a subcutaneous sensor to sense and monitor the amount of glucose in interstitial fluid of the patient 100 and communicates corresponding data to the diabetes manager 104.

The diabetes manager 104 can perform various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives glucose levels of the patient 100 from the CGM patch 200, or data from which glucose levels of the patient 100 may be computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a determined amount.

Figure 2:
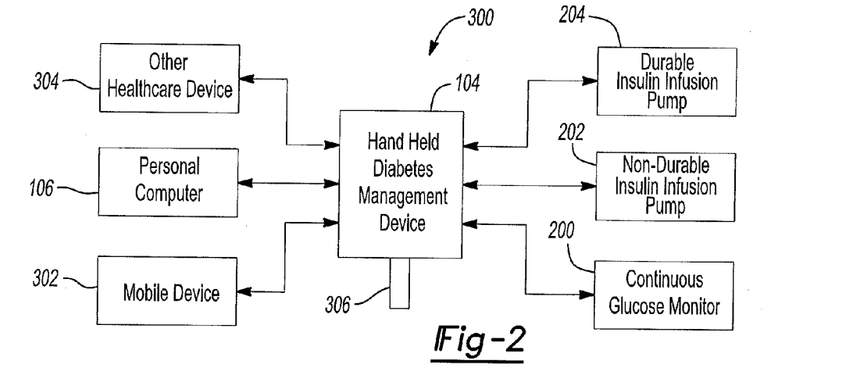
FIG. 2 shows a diabetes management system used by patients and clinicians to manage diabetes.

Generally, and referring now to FIG. 2, a diabetes management system 300 used by the patient 100 and the clinician can include one or more of the following devices: the diabetes manager 104, the continuous glucose monitor (CGM patch) 200, the insulin pump 202 or 204, a mobile device 302, the PC 106 with diabetes analysis and/or configuration software, and other healthcare devices 304. The diabetes manager 104 can be configured as a system hub that communicates with the devices of the diabetes management system 300. Alternatively, the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard, as extended using guidelines provided by Continua® Health Alliance Design Guidelines. Further, healthcare records systems such as Microsoft® HealthVault™ and Google™ Health can be used by the patient 100 and clinician to exchange information.

The diabetes manager 104 can receive glucose readings from one or more sources (e.g., from the CGM patch 200). The CGM patch 200 regularly monitors the interstitial glucose level of the patient 100. The CGM patch 200 periodically communicates glucose levels to the diabetes manager 104. The diabetes manager 104 and the CGM patch 200 communicate wirelessly using generally a wireless protocol, such as, for example, the standard Bluetooth Low Energy wireless protocol. Any other suitable wireless protocol can be used instead.

Additionally, the diabetes manager 104 includes a blood glucose meter (BGM) and a port that communicates with the BGM (not shown). The port can receive a blood glucose measurement strip 306. The patient 100 deposits a sample of blood on the blood glucose measurement strip 306. The BGM analyzes the sample and measures the blood glucose level in the sample. The blood glucose level measured from the sample is used to determine the amount of insulin to be administered to the patient 100 using, for example, the insulin pump 202, 204.

The diabetes manager 104 also communicates with the insulin pump 202 or 204. The insulin pump 202 or 204 can be configured to receive instructions from the diabetes manager 104 to deliver a predetermined amount of insulin to the patient 100 in the form of basal dose or bolus dose. Additionally, the insulin pump 202 or 204 can receive other information including meal and/or exercise schedules of the patient 100. The insulin pump 202 or 204 or the diabetes manager 104 can determine the amount of insulin to administer based on the additional information as a basal dose or bolus dose.

The insulin pump 202 or 204 can also communicate data to the diabetes manager 104 via wireless communication module including, for example, a pump transceiver or a communications radio. The data can include amounts of insulin delivered to the patient 100, corresponding times of delivery, and pump status. The diabetes manager 104 and the insulin pump 202 or 204 can communicate using a wireless communication protocol such as Bluetooth. Other wireless communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continua® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other wireless interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth or another suitable wireless communication protocol. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 3:
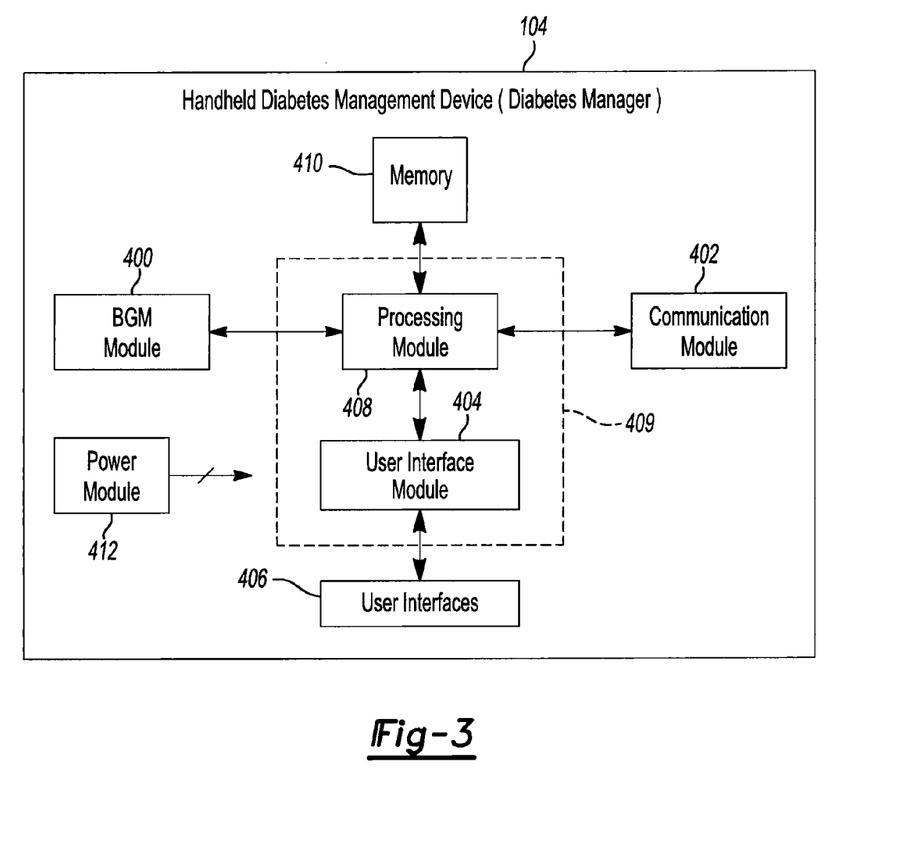
FIG. 3 is a functional block diagram of a diabetes manager according to the present teachings.

Referring now to FIG. 3, the diabetes manager 104 includes a blood glucose measuring (BGM) module 400, a communication module 402, a user interface module 404, various user interface elements 406, a processing module 408, a memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and measures the amount of blood glucose in the samples. The communication module 402 can include a transceiver and/or multiple radios that communicate with different devices of the diabetes management system 300. The user interface module 404 interfaces the diabetes manager 104 to various user interface elements 406 that the patient 100 can use to interact with the diabetes manager 104. For example, the user interface elements 406 can include a touchscreen or other display, touchscreen or other keys, switches, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interface elements 406 via the user interface module 404. The processing module 408 outputs data to and receives data from the devices of the diabetes management system 300 via the communication module 402. The power module 412 supplies power to the components of the diabetes manager 104. The power module 412 can include a rechargeable battery. The battery can be charged via the USB port of the diabetes manager 104 using an adapter that plugs into a wall outlet or using a cable that plugs into a PC.

Figure 4:
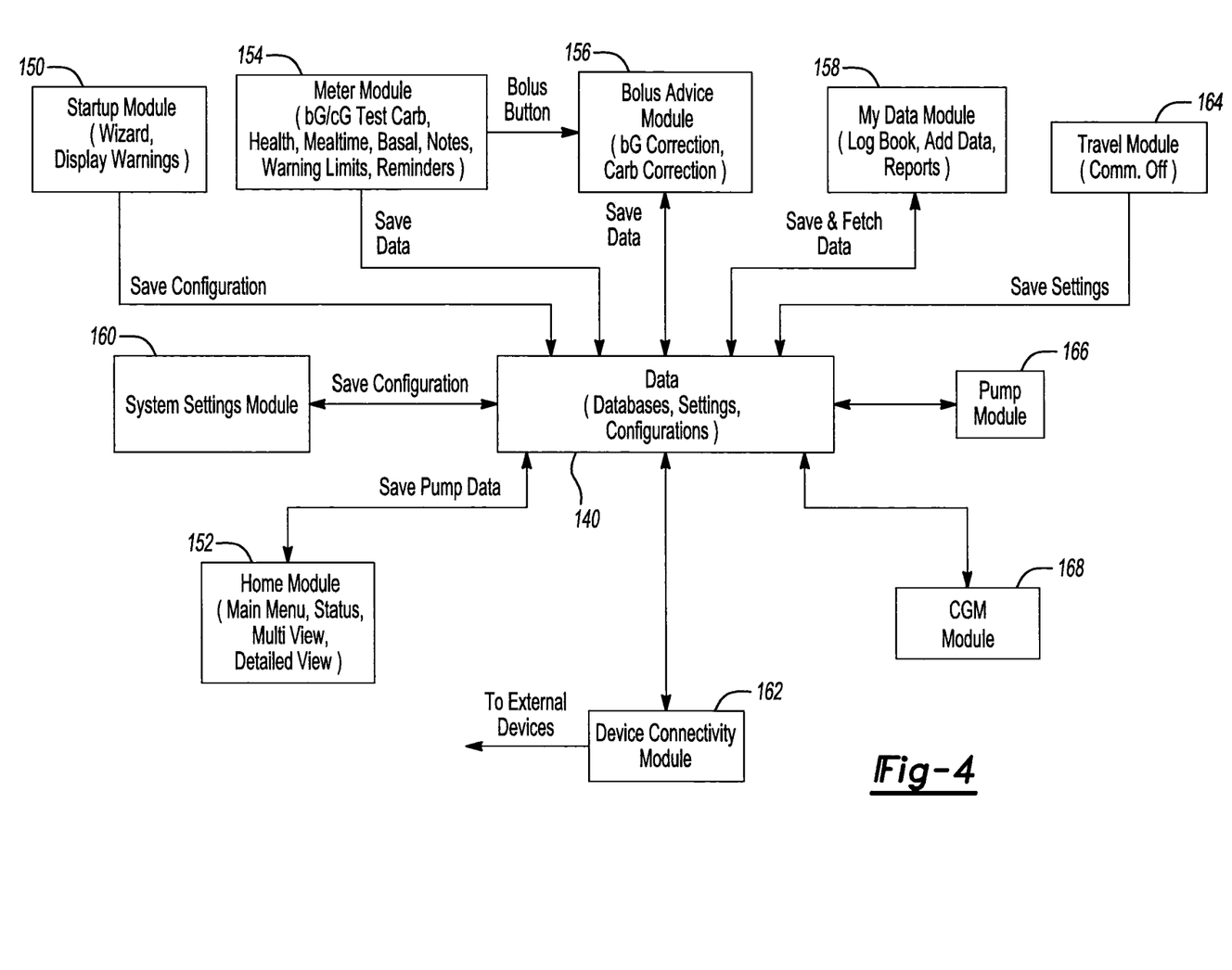
FIG. 4 is a block diagram illustrating a user interface with a travel module for a diabetes manager according to the present teachings.

Referring to FIG. 4, a logical navigation architecture of the user interface module for handheld diabetes manager 104 is illustrated. The following modules can be integrated in the navigation architecture of the handheld diabetes manager 104: a startup module 150, a home module 152, a meter module 154, a bolus advice module 156, a "my data" module 158, a system settings module 160, a device connectivity module 162, a travel module 164, a pump module 166 and a data module 140. The data module 140 includes databases, settings and configurations, and acts as a central hub that communicates with the other modules to store and provide information regarding data, settings, configuration related to the other modules. In some embodiments, some of the modules can be removed or inactivated or additional modules can be added. For example, the pump module 166 may be removed or inactivated in models of the handheld diabetes manager 104 for non-pump users. In other modules, a continuous glucose monitoring module (CGM) 168 can be added, as illustrated in dashed lines.

As briefly outlined in reference to FIG. 4, the handheld diabetes manager 104 of the present teachings integrates in a single handheld device various functions, controls, calculations, tests and reports that, in prior art devices, are typically split among different specialized devices, such as single-purpose bG meters, single-purpose remote devices for insulin pumps and other similar single or limited-purpose diabetes managers. Integrating the multiple tasks and functions of the plurality of modules of the handheld diabetes manager 104 of the present teachings requires a user interface that does not simply superpose various functions in an additive manner, but anticipates behaviors and use case scenarios that are unique and emerge from the interaction of the multiplicity of modules when all these modules are integrated in the same handheld device. Such interactions arise not just from the hardware aspects of the device, but from the various possibilities or use scenarios that a user may subject the device based on the user-perceived and/or actual capabilities of the device. For example, although portability is common to many prior art diabetes devices, portability and use in restricted or semi-restricted environments, such as during air travel, requires anticipation of alternative use case or use scenarios to avoid conflicts, without totally disabling the device. In the following example, the term pump is used interchangeably for an insulin pump, a micropump, and insulin patch with a CGM device or a combination, unless differentiation is required.

In the context of the user interface for the handheld diabetes manager 104, a use case is an observable result based upon an action by a user. A use case describes the behavior and navigation along a primary or alternate path including any standard business rules for diabetes management and is graphically represented in an activity or behavior diagram, as shown, for example, in FIG. 5.

Referring to FIG. 4, the present teachings are directed generally to the travel module 164 of the user interface. Generally, the travel module 164 interacts with the meter module 154, the bolus advice module 156 and pump module 166 (and/or the CGM module 168). The travel module 164 can be accessed, for example, via a travel/flight mode button 688 of a main menus screen 660, shown in FIG. 8A and described below. The bolus advice module 156 receives blood glucose measurements from the blood glucose measurement module 400 (FIG. 3) and determines various insulin recommendations in the form of a bolus for a patient based in part on the blood glucose measurements, meals, lifestyle factors, health events, etc.

Figure 5:
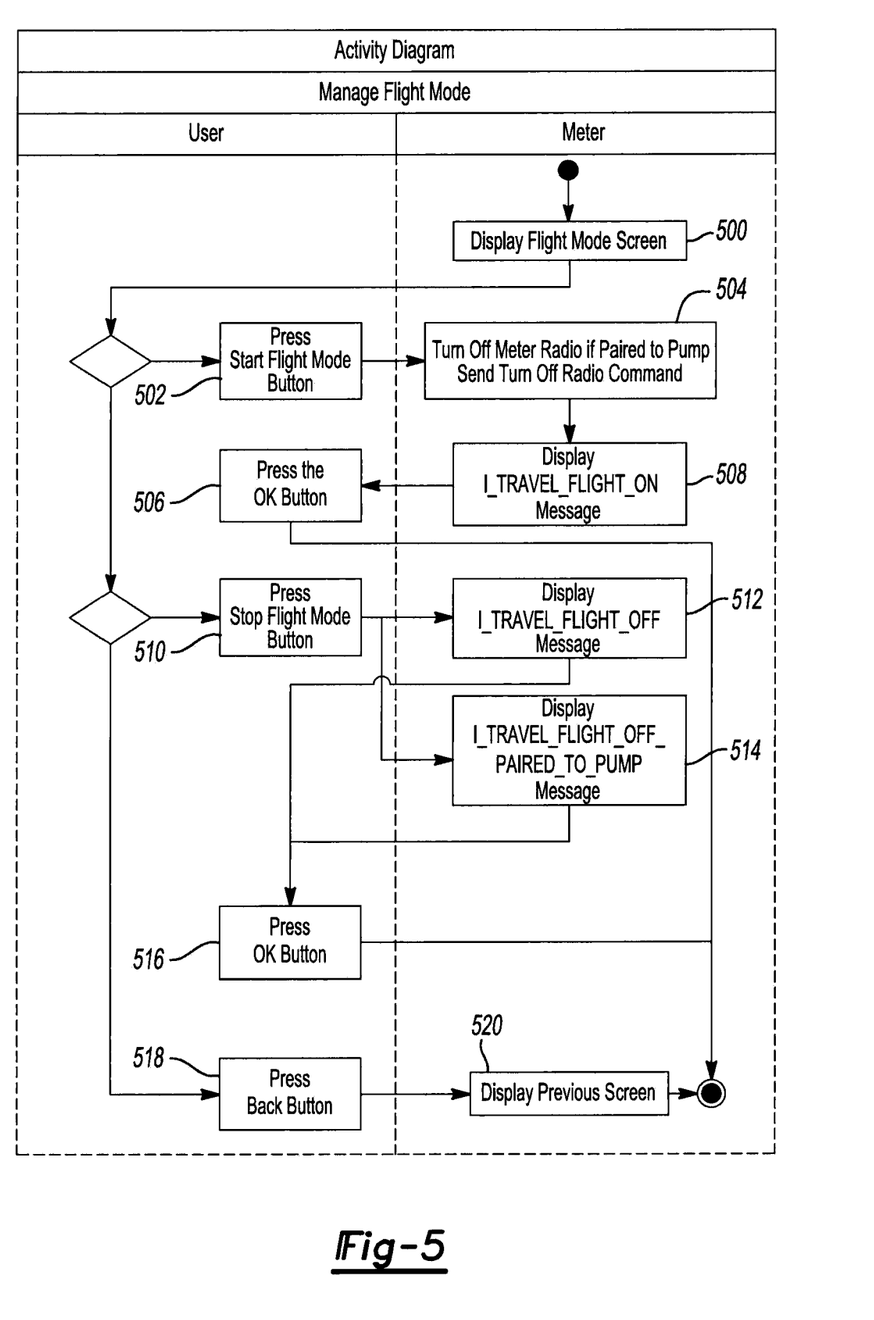
FIG. 5 is an activity diagram illustrating behavior flow for managing a flight mode according to the present teachings.

Referring to FIG. 5, an activity diagram of behavioral flow for the travel module 164 is illustrated. From a home screen or a main screen 660 (FIG. 8A), the flight mode button 688 (FIG. 8A) can be selected to display flight mode screen (block 500) that includes a button to start flight mode, a button to stop flight mode and a button to go back. Pressing the start flight mode button (block 502), the wireless communication with an external medical device, such as the insulin pump 202, 204 or CGM 200 that is paired with the diabetes manager 104 and currently communicating with the diabetes manager 104, will be stopped. Specifically, if the insulin pump 202, 204 is paired and currently communicating with the diabetes manager 104, the diabetes manager 104 will send a command via the communications module 402 (block 504) to the insulin pump 202, 204 (or other external medical device) to turn off the pump's wireless radio or transceiver and stop the communication. When the diabetes manager 104 sends a command to the pump 202, 204 to turn the radio off and in response an error is received from the pump 202, 204, a warning message that the flight mode failed at the pump will be displayed 202, 204. The diabetes manager 104 will also disable the diabetes manager's 104 own wireless communication, such as turn off Bluetooth radio, for example. If the diabetes manager 104 is not set up to communicate with an external medical device, pressing the start flight mode button (block 502) will simply disable the diabetes manager's 104 own wireless communication. The diabetes manager 104 displays a screen with a notification that the travel/flight mode is on (block 508). If the diabetes manager 104 is paired with the pump 202, the notification also includes a "paired to pump" text message. Additionally, the start flight mode button (block 502) is disabled and grayed out and the stop flight mode button is enabled (block 510). Pressing a confirming or OK button (block 506) returns the diabetes manager 104 to the previous screen (block 520).

With continued reference to FIG. 5, pressing the stop flight mode button (block 510) while flight mode is enabled, enables the wireless communication and displays a screen with the notification that the travel/flight mode is off (block 512). If the insulin pump 202, 204 is paired with the diabetes manager 104, a notification that the travel/flight mode is off and that the pump is paired will be displayed (block 514). Pressing an OK button (block 516) from the travel mode screens (blocks 512 and 514) displays the previous screen (block 520). Pressing a back button (block 518) from the flight mode screen (block 500) will also display the previous screen (block 520).

Figures 8A, 8B:
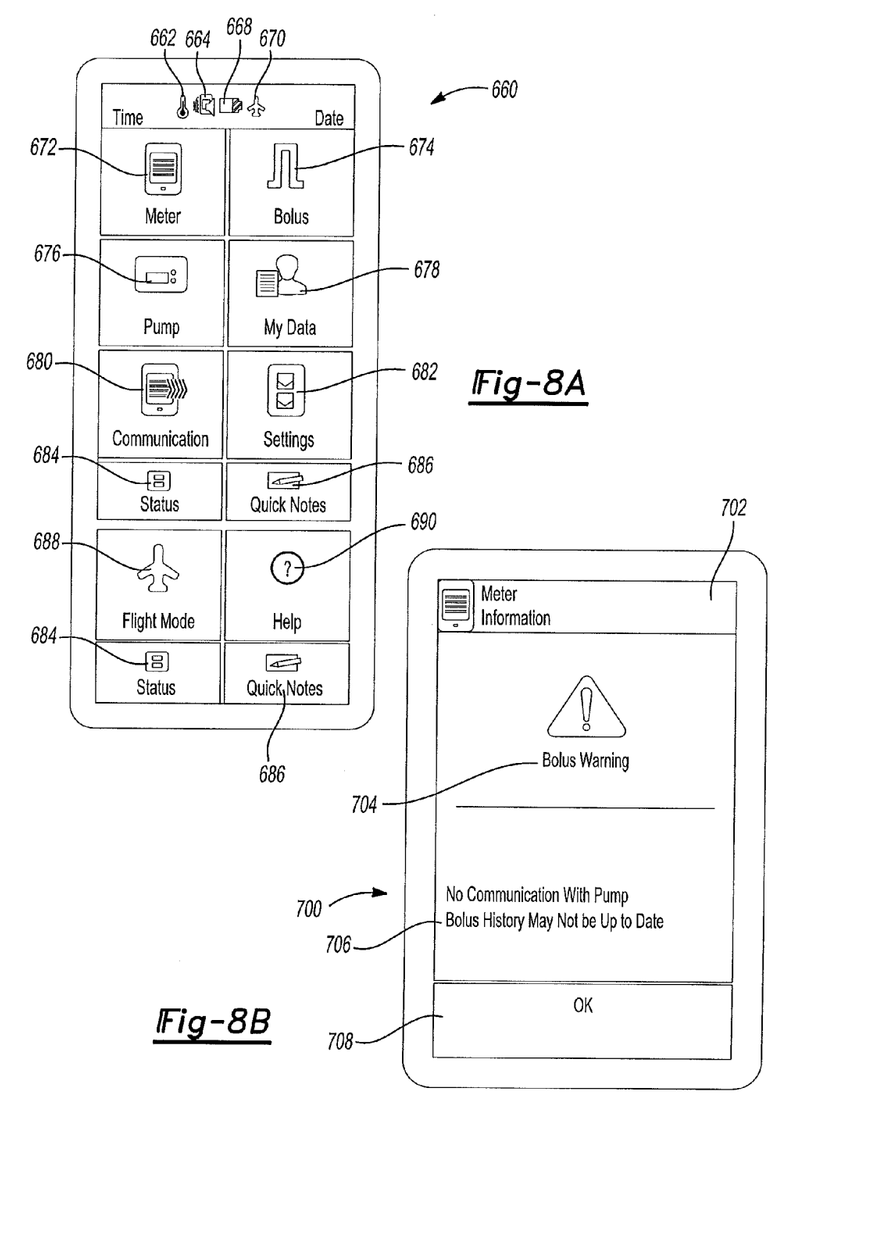
FIG. 8A illustrates an exemplary main menu screen of a diabetes manager according to the present teachings.
FIG. 8B illustrates a representative screen illustrating a bolus warning when the flight mode is turned on according to the present teachings.
Figure 8C:
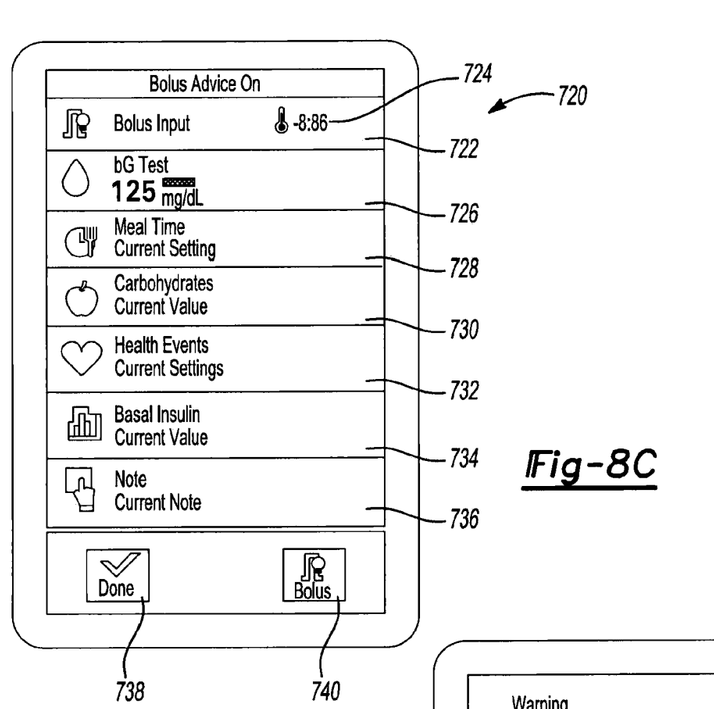
FIG. 8C illustrates a representative screen showing a detailed screen for bolus advice according to the present teachings.
Figure 8D:
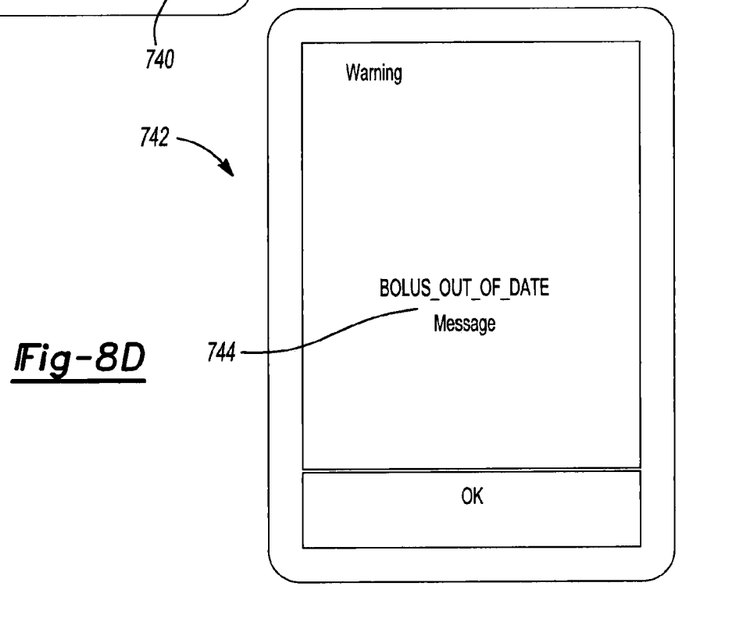
FIG. 8D illustrates a representative screen showing a bolus advice warning when the flight mode is turned on according to the present teachings.
Figure 9:
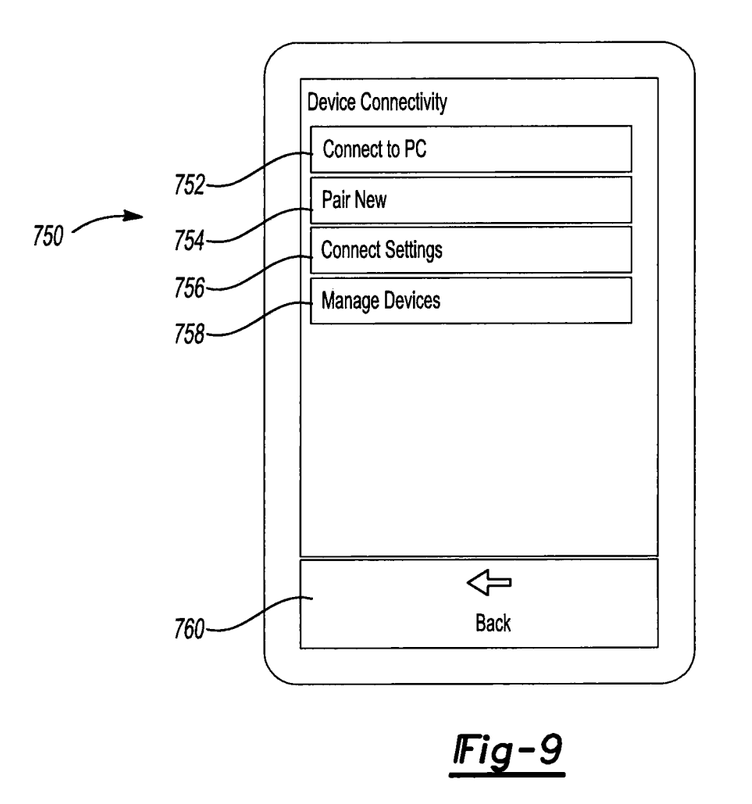
FIG. 9 illustrates a representative screen showing device connectivity according to the present teachings.

Referring to FIG. 8A, a main menu screen 660 can display time and date information, and various status icons, such as, for example a temperature icon 662, sound icon 664 (including vibrate mode), battery status icon 668 and flight mode icon 670. Some status icons are only displayed when they are enabled or active. For example, if flight mode is enabled, the flight mode icon 670 is displayed. Similarly, the sound and sound/vibrate icons 664 are displayed when the corresponding functions are enabled. The temperature icon 662 is displayed when the diabetes manager 104 detects that the temperature is outside a bG test warning temperature or a bG test lockout range, as defined by a code key for the test strip 306. The battery icon 668 displays the current charge condition of the battery. The main menu screen 660 includes various buttons (mechanical or touch buttons) that can be activated by touch or stylus or other selector device to display a corresponding detailed screen. The button labeled meter 672 represents a graphical user interface for the meter module 154 and interfaces with the BGM module 400. The button labeled pump 676 illustrates a graphical user interface for an external medical device, in this case a pump, as shown in the pump module 166 (FIG. 4) and in FIG. 2 at 202 and 204. The pump button 676 is used to represent graphically any such external medical device, with the insulin infusion pumps 202, 204 and the CGM patch 200 being exemplary external medical devices.

With continued reference to FIG. 8A, the main menu screen 660 can include a bolus button 674 corresponding to the bolus advice module 156, a "my data" button 678 corresponding to the "my data" module 158, a communications button 680 corresponding to the "device connectivity" (or communications) module 162, and a settings button 682 corresponding to the system setting module 160. The main menu screen 660 can also include a status button 684, and a quick notes button 686. A flight mode button 688 and a help button 690 (indicated as a question mark) can be presented and accessed by swiping the screen along its length to shift the buttons on the main menu screen 660. Some of the preceding set of buttons may go out of view as a result.

Figures 6, 7:
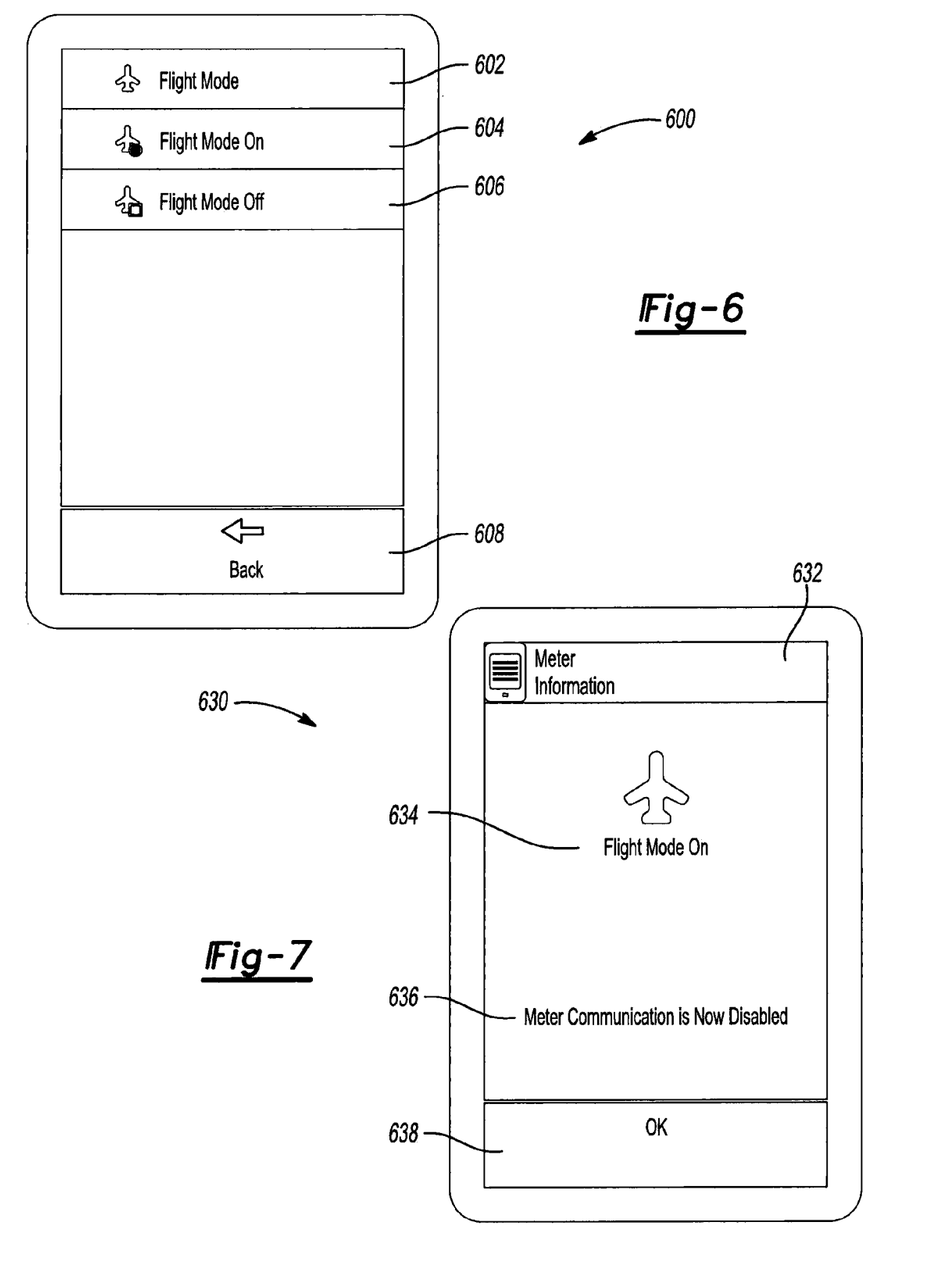
FIG. 6 illustrates a representative flight mode screen according to the present teachings.
FIG. 7 illustrates a representative screen indicating that flight mode is turned on according to the present teachings.

Referring now to FIGS. 6-9, pressing the flight mode button 688 from the main menu screen 660 (FIG. 8A) displays a flight mode screen 600 (FIG. 6) indicating the current status of the flight mode. The flight mode screen 600 includes a "flight mode" heading 602, a "flight mode on" button 604 and a "flight mode off" button 606. If flight mode is enabled, pressing the flight mode on button 604 displays a flight mode on screen 630 (FIG. 7). The flight mode on screen 630 can display a "meter information" heading 632, a flight mode on icon and text at 634 and a text message that meter communication is disabled at 636. Pressing an OK button 638 displays the main menu screen 660. Similarly, if flight mode is not enabled, a screen indicating that the flight mode is off will be displayed (not shown). From the main menu screen 660, pressing the bolus button 674, displays a bolus advice screen. When bolus advice has been programmed in the diabetes manager 104 and set to on status (bolus advice on), the bolus advice screen 720 of FIG. 8C is displayed. Screen 720 includes a heading 722 labeled bolus input with a bolus on icon and temperature icon, and various bolus-related buttons that when pressed display more detailed screens. These buttons include a bG test button 726, a meal time button 728, a carbohydrates button 730, a health events button 732, a basal insulin button 734, and note button 736. Pressing a confirming button 738 displays the previous screen. Pressing a bolus button 740 while in flight mode will display a warning screen 742 (FIG. 8D) with the message that bolus information may be out of date. Similarly, pressing the meter button 672 from the main menu screen 660 while in flight mode will display a warning screen 742 (FIG. 8D) with the message that bolus information may be out of date.

Referring to FIG. 8B, pressing the bolus button 674 while in flight mode displays a screen 700 having a meter information heading 702 and displaying a bolus warning message at 704 and a text message 706 that there is no communication with the pump and that the bolus history may be out of date. Pressing an OK button 708 displays the previous screen. The warning screens 700 and 742 of FIGS. 8B and 8D may be also displayed from other screens when the user attempts to access information related to the current status of the bolus and bolus history.

When the flight mode is on, the pump button 676 in the main screen 660, and in any other detailed or status screen where it may be displayed, is disabled and grayed out. Additionally, in flight mode, connectivity to a PC and pairing with devices, and corresponding connectivity buttons are disabled. For example, in the device connectivity screen 750 of FIG. 9, a "manage paired devices" button 758 is disabled and grayed out. Similarly, a pair new devices button 754 for pairing new devices is also disabled and grayed out. Other buttons, such as a connect settings button 756 and a "connect to PC" button 752 can remain enabled in the connectivity screen 750. The device connectivity screen 750 is displayed, for example, by pressing the communications button 680 of the main menu screen 660. Additionally, when the flight mode is on, only status screens with bG status information are displayed. Any status screens that include pump (or other external medical device) status are either not displayed or the pump information is suppressed or grayed out.

Figure 10:
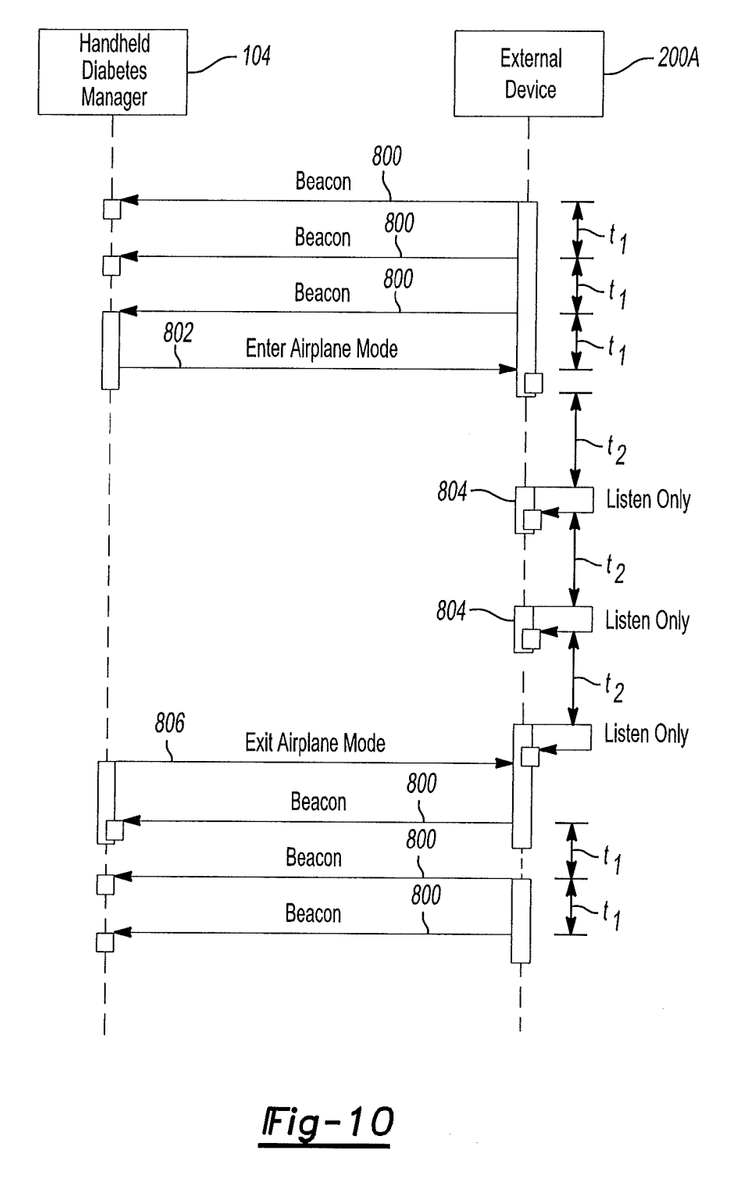
FIG. 10 is an activity diagram illustrating an alternative embodiment for managing a flight mode according to the present teachings.

Referring to FIG. 10, an alternative embodiment for managing a flight mode is diagrammatically illustrated. In this embodiment, the handheld diabetes manager 104 can communicate with an external medical device 200A, such as an insulin pump 202, 204 or a CGM patch 200 using radio frequency signals at periodic intervals. Specifically, during usual, non-flight mode, the external medical device 200A and the diabetes manager 104 can communicate with signals (beacon or notification or advertisement signals) 800 initiated and emitted by the external medical device 200A at periodic intervals of time $t_1$. The external medical device 200A then listens for a response or message from the diabetes manager 104 during a short, predetermined listening interval or window. Accordingly, the diabetes manager 104 can communicate with the external medical device 200A during the external medical device's listening period after a beacon 800 is sent. If the listening window associated with a specific beacon is missed, the diabetes manger 104 can communicate with the external medical device 200A during the next listening window. This arrangement conserves power in the external medical device 200A, which typically has greater power constraints than the diabetes manager 104.

To enter flight mode, the diabetes manager sends a command or message 802 to the external medical device 200A to enter a flight or airplane mode during its regular listening window. The external medical device 200A is programmed such that upon receiving the message 802 it enters a flight mode that includes listening only windows 804 at periodic intervals $t_2$ that are typically greater than the regular interval $t_1$. No beacons 800 are transmitted while the external medical device 200A is in flight mode. When it is determined that flight mode can be safely exited, the diabetes manager 104 sends a command 806 to the external medical device 200A during one of its listening windows and instructs the external medical device 200A to resume a regular non-flight mode. Alternatively, a specific time interval after which the external medical device 200A can exit the flight mode can be sent to the external medical device 200A together with the initial command 802 to enter the flight mode. Typically, the interval for exiting flight mode is set for the known duration of the flight and possibly an additional safety interval. After exiting the flight mode, the external medical device 200A then resumes the transmission of beacons 800 at regular periodic intervals $t_1$.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer-readable medium. The computer programs may also include stored data. Non-limiting examples of the non-transitory tangible computer readable medium are nonvolatile memory, magnetic storage, and optical storage.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A diabetes management system including a handheld diabetes manager having a flight mode that cooperatively having a flight mode that cooperatively interacts with an external medical device and the external medical device being physically separated from the handheld diabetes manager, the handheld diabetes manager comprising:
   a port formed in a housing of the handheld diabetes manager and configured to receive a test strip;
   a blood glucose measurement module residing in the housing and cooperatively operable with the test strip inserted in the port for blood glucose measurement;
   a display integrated into the housing;
   a user interface module programmed to generate a graphical user interface on the display, wherein the graphical user interface includes a selector for enabling or disabling a flight mode and the user interface module is implemented by computer readable instructions executed by a processor in the handheld diabetes manager;
   a communication module configured to selectively communicate via a wireless data link with the external medical device, wherein the communication module is powered on by the user interface module in response to an indicator from the user interface module that the flight mode is disabled and is powered down by the user interface module in response to an indicator from the user interface module that the flight mode is enabled; and
   wherein the communication module is further configured to determine whether the handheld diabetes manager is paired with the external medical device and, in response to the indicator that the flight mode is enabled and a determination that the diabetes manager is paired with the external medical device, sends a flight mode command via the wireless data link to the external medical device, where the flight mode command includes a time interval after which the external medical device can resume communication with the diabetes manager.

2. The diabetes manager of claim 1, further comprises an external medical device in the form of an insulin pump.

3. The diabetes manager of claim 1, wherein the external medical device is a continuous glucose monitoring device.

4. The diabetes manager of claim 1, wherein the graphical user interface includes a connectivity screen with inputs for pairing new devices with the diabetes manager and the user interface module, in response to the indicator that flight mode is enabled, disables pairing of new devices and grays out the inputs for pairing new devices on the connectivity screen.

5. The diabetes manager of claim 1, wherein the graphical user interface includes a connectivity screen with inputs for managing new devices and the user interface module, in response to the indicator that flight mode is enabled, disables management of new devices and grays out the inputs for managing new devices on the connectivity screen.

6. The diabetes manager of claim 1, wherein the user interface module operates to display a warning on the graphical user interface in response to an error message received from the external medical device, where the error message is sent by the external medical device in reply to the turn off command received from the diabetes manager.

7. The diabetes manager of claim 1, wherein the user interface module displays a warning on the graphical user interface in response to a request for bolus advice and the indicator that flight mode is enabled.

8. The diabetes manager of claim 1, wherein the user interface module displays an icon that flight mode is enabled on the graphical user interface in response to the indicator that flight mode is enabled.

9. The diabetes manager of claim 8, wherein the user interface module displays a notification on the graphical user interface in response to the indicator that flight mode is enabled and the determination that the handheld diabetes manager is paired with the external medical device, where the notification indicates pairing information for the handheld diabetes manager and the external medical.

* * * * *

UNITED STATES PATENT AND TRADEMARK OFFICE
CERTIFICATE OF CORRECTION

PATENT NO.         : 9,264,129 B2                                               Page 1 of 1
APPLICATION NO.    : 13/661156
DATED              : February 16, 2016
INVENTOR(S)        : Mark G. Mears et al.

It is certified that error appears in the above-identified patent and that said Letters Patent is hereby corrected as shown below:

In the Specification

Column 2
Line 63                       before "recommendations", insert --bolus advice
                              and while the flight mode is enabled, a notification
                              on the display that an insulin--.

In the Claims

Column 11
Line 13, claim 1              after "cooperatively", delete "having a flight mode
                              that cooperatively"

Signed and Sealed this
Fourteenth Day of June, 2016

Michelle K. Lee
*Director of the United States Patent and Trademark Office*